US006974586B2

(12) United States Patent
Greenhalgh et al.

(10) Patent No.: US 6,974,586 B2
(45) Date of Patent: Dec. 13, 2005

(54) SUPPORTED LATTICE FOR CELL CULTIVATION

(75) Inventors: E. Skott Greenhalgh, Wyndmoor, PA (US); Carol A. Kaufmann, Philadelphia, PA (US)

(73) Assignee: Secant Medical, LLC, Perkasie, PA (US)

( * ) Notice: Subject to any disclaimer, the term of this patent is extended or adjusted under 35 U.S.C. 154(b) by 491 days.

(21) Appl. No.: 09/998,880

(22) Filed: Oct. 31, 2001

(65) Prior Publication Data

US 2002/0066360 A1 Jun. 6, 2002

Related U.S. Application Data

(60) Provisional application No. 60/244,491, filed on Oct. 31, 2000.

(51) Int. Cl.$^7$ ............................. A61F 2/00; C12N 11/02; C12N 11/08; C12N 5/06; C12N 5/08
(52) U.S. Cl. ................. 424/423; 435/177; 435/180; 435/395
(58) Field of Search .................... 424/423, 93.7; 435/174, 177, 180, 395

(56) References Cited

U.S. PATENT DOCUMENTS

| 5,674,277 | A | | 10/1997 | Freitag ........................... 623/1 |
| 5,718,159 | A | * | 2/1998 | Thompson ....................... 87/33 |
| 5,759,830 | A | | 6/1998 | Vacanti et al. ............... 435/180 |
| 5,891,191 | A | * | 4/1999 | Stinson ........................ 623/1.2 |
| 6,022,743 | A | | 2/2000 | Naughton et al. ........... 435/395 |
| 6,123,115 | A | | 9/2000 | Greenhalgh ............... 139/196.1 |
| 6,156,064 | A | | 12/2000 | Chouinard ..................... 623/1 |
| 6,534,084 | B1 | * | 3/2003 | Vyakarnam et al. ......... 424/443 |
| 6,551,352 | B2 | * | 4/2003 | Clerc et al. .................. 623/1.2 |

* cited by examiner

*Primary Examiner*—David M. Naff
(74) *Attorney, Agent, or Firm*—Synnestvedt & Lechner LLP

(57) ABSTRACT

A supported lattice is disclosed having a support substrate formed of a plurality of resilient filamentary members braided together to yield a coarse mesh having relatively large interstices and a cell cultivation lattice formed of a plurality of flexible filamentary members braided together and with the resilient filamentary members to form a fine mesh having small interstices. The cell cultivation lattice provides a bed adapted for growing cells in a two-dimensional array across the large interstices of the support substrate to form a continuous surface of living tissue useful to form a graft.

16 Claims, 6 Drawing Sheets

FIG.6
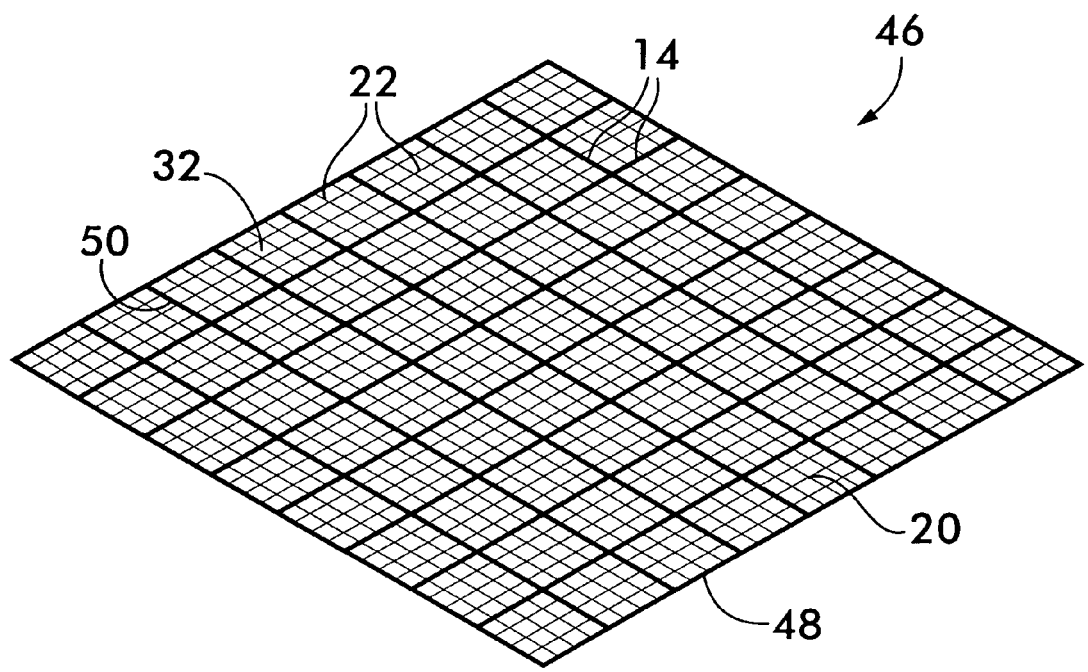
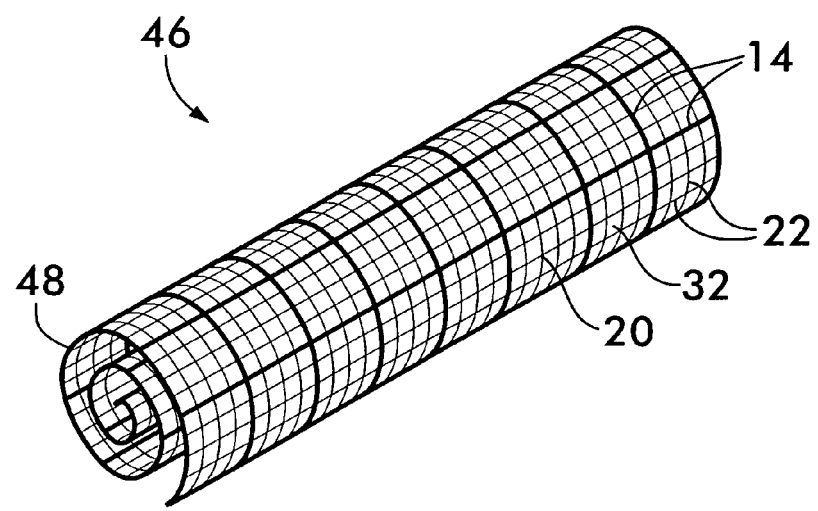
FIG.7

SUPPORTED LATTICE FOR CELL CULTIVATION

RELATED APPLICATION

This application is based on and claims priority of U.S. Provisional Patent Application No. 60/244,491, filed Oct. 31, 2000.

FIELD OF THE INVENTION

This invention concerns a supported lattice for cultivating living cells to form living tissue for use in surgical implants as grafts to heal damaged tissue and to correct various disorders.

BACKGROUND OF THE INVENTION

Various medical procedures, in particular, surgical procedures, involve the repair of diseased or damaged tissue by replacing the tissue with a graft. The graft may be natural, synthetic or a combination of the two. Examples of current procedures involving grafts are described below, along with certain short comings associated with each.

Coronary Artery Bypass

Coronary artery bypass grafting is a procedure used in the treatment of ischemic heart disease wherein the heart receives insufficient oxygen. Most often, ischemia is caused by atherosclerotic disease of the epicardial coronary arteries wherein the lumen of these vessels is reduced in size, reducing and/or limiting the flow of blood to the heart. In the bypass procedure, a section of vein, usually taken from the leg of the patient, is used to form a connection between the aorta and the coronary artery distal to the obstructive region, thus, restoring adequate blood flow.

While the operation is considered to be relatively safe, significant trauma is experienced by the patient in the harvesting of the vein which is used to effect the connection in the operation. Natural veins are currently preferred over synthetic grafts because it is very difficult to form a vessel suitable for use in bypass operations which remains unobstructed. The inner diameter of such veins is on the order of 6 mm, and synthetic grafts of this size are currently unacceptable because they are subject to occlusions due to collapse and clotting.

There is clearly a need for a graft having a small diameter lumen useable in bypass operations instead of a natural vein in order to avoid the trauma associated with harvesting the vein from the patient.

Repair of Severed Nerve Ganglia

When nerve ganglia are severed, as, for example, in an injury, a piece of the nerve is often destroyed in the process, leaving a severed nerve having two nerve endings which should be connected. It is sometimes possible to reconnect the severed nerve endings by stretching the ends and suturing them together. However, this technique is only effective if the nerve endings are separated by 3 mm or less. When the separation distance is greater than 3 mm, they cannot be successfully stretched to make up the separation distance. Instead, the ends are encouraged to grow together. However, muscle and other tissue near the injured nerves tends to interfere with the growth of the ganglia. It would be advantageous to provide a temporary graft which would encourage the growth of the nerve cells and prevent interference by nearby tissue.

Skin Grafts

Skin which is damaged by heat, abrasion, ulcerations or wounds is sometimes repairable by removing skin from one part of the body to serve as a graft on the injured part. However, this requires that the patient undergo the trauma of harvesting the graft, creating yet another region of the body which is subject to infection and which must be allowed to heal. Skin grafts which do not require harvesting of skin from another part of the body would provide significant improvement to the treatment of damaged skin tissue.

Hernia Operations

A hernia is the protrusion of a loop of an organ or tissue through an abnormal opening, for example, a protrusion of loops of the intestines through the abdominal wall. Current techniques for repair of a hernia involve invasive surgery to implant a graft to repair and strengthen the abnormal opening in the wall. Grafts currently used in this operation tend to be extremely flexible and are not, therefore, suitable for manipulation via less invasive laparoscopic techniques. Treatment of hernias would be improved significantly by the development of grafts which could be laparoscopically positioned and attached in order to eliminate the need for the trauma normally associated with the surgery.

SUMMARY AND OBJECTS OF THE INVENTION

The invention concerns a supported lattice for cultivating living cells to form living tissue. The supported lattice comprises a support substrate comprising a plurality of resilient filamentary members interlaced together. The resilient filamentary members are interlaced to form a relatively coarse mesh defined by relatively large interstices between the resilient filamentary members. The supported lattice further includes a cell cultivation lattice also comprising a plurality of flexible filamentary members interlaced with one another and with the resilient filamentary members. The flexible filamentary members are interlaced to form a relatively fine mesh defined by relatively small interstices between the flexible filamentary members and adapted for growing cells in a two-dimensional array across the large interstices of the support substrate to form a substantially continuous surface comprising the living tissue.

The supported lattice may take one of a number of configurations, the filamentary members being conveniently braided into an elongated tube, for cultivating blood vessels for example. To cultivate the various different layers of cells comprising tissue such as a blood vessel, the supported lattice further comprises a second elongated tube positioned coaxially within the first elongated tube. The second elongated tube comprises a second support substrate comprising a plurality of second resilient filamentary members interlaced together, the second resilient filamentary members being interlaced to form a relatively coarse mesh defined by relatively large interstices between the second resilient filamentary members. A second cell cultivation lattice is supported on the second support lattice, the second cell cultivation lattice comprising a plurality of second flexible filamentary members interlaced with one another and the second resilient filamentary members. The second flexible filamentary members are interlaced to form a relatively fine mesh defined by relatively small interstices between the second flexible filamentary members and adapted for growing cells in a two-dimensional array across the large interstices of the second support substrate to form a second substantially continuous surface comprising the living tissue.

The invention further includes a method of making a supported lattice adapted for growing cells in a two-dimensional array to form a substantially continuous surface comprising living tissue. The method comprises the steps of:

(1) braiding a plurality of resilient filamentary members into a tubular support substrate comprising a relatively coarse mesh defined by relatively large interstices between the resilient filamentary members, the resilient filamentary members comprising a heat-shrinkable material;

(2) braiding a plurality of relatively flexible filamentary members with one another and with the resilient filamentary members to form a lattice supported on the support substrate and comprising a relatively fine mesh defined by relatively small interstices between the resilient filamentary members, the flexible filamentary members comprising a dimensionally stable material having a higher melting temperature than the heat-shrinkable material;

(3) compressing the tubular support substrate longitudinally causing the flexible filamentary members to buckle and form dimples located within the interstices of the support substrate;

(4) heating the filamentary members above the melting temperature of the heat-shrink material thereby shrinking the resilient filamentary members and fusing them together with the flexible filamentary members at mutual points of contact.

It is an object of the invention to provide a lattice for the cultivation of living cells to form living tissue.

It is another object of the invention to provide a lattice for the cultivation of living cells in a two-dimensional array to form a substantially continuous surface comprising living tissue.

It is yet another object of the invention to provide a lattice for the cultivation of living cells which can be formed into a tube.

It is again another object of the invention to provide a lattice structure which can grow multiple layers of cells in a two-dimensional array to form a substantially continuous surface comprising multi-layer living tissue.

These and other objects and advantages of the invention will become apparent upon consideration of the following drawings and detailed description of preferred embodiments.

BRIEF DESCRIPTION OF THE DRAWINGS

FIG. 6 shows a perspective view of a supported lattice having a planar shape; and FIG. 7 shows a perspective view of the supported lattice shown in FIG. 6, rolled into a spiral shape.

DETAILED DESCRIPTION OF PREFERRED EMBODIMENTS

Examples of various presently preferred embodiments of the supported lattice for cultivation of living cells are provided below in the context of various surgical procedures in which they may be used. It is to be understood that the various examples of the invention described below are for illustration only and are in no way intended to limit the invention or its uses.

Tubular Supported Lattice for Coronary Bypass Graft

Figure 1:
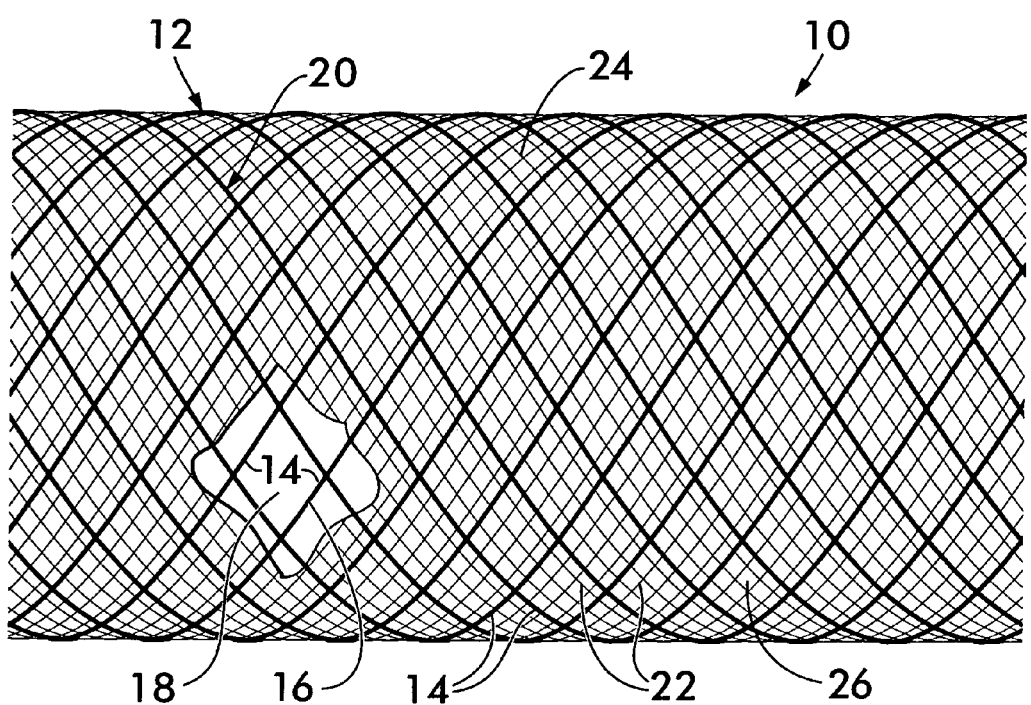
FIG. 1 shows a side view of a tubular supported lattice for cultivating living cells according to the invention.

FIG. 1 shows a tubular supported lattice 10 comprising a support substrate 12 formed of a plurality of resilient filamentary members 14 interlaced together. The resilient filamentary members 14 are interlaced to form a relatively coarse mesh 16 defined by relatively large interstices 18 formed between the resilient filamentary members 14. Interstices 18 are considered large relative to the living cells to be cultivated, such that while cells may grow along and around the resilient filamentary members they will not tend to bridge the interstices and grow across the support substrate. Filamentary members 14 are intended primarily to provide support and maintain the desired tubular shape.

A cell cultivation lattice 20 is supported on the support substrate 12. Preferably, cell cultivation lattice 20 is formed of a plurality of flexible filamentary members 22 interlaced with one another and with the resilient filamentary members 14 comprising the support substrate. Flexible filamentary members 22 are interlaced to form a relatively fine mesh 24 defined by relatively small interstices 26. Mesh 24 generally occupies the interstices 18 of the support substrate 12. Interstices 26 are small relative to the interstices 18 and mesh 24 provides a bed adapted for growing living cells in a two-dimensional array across the cell cultivation lattice 20 to form a substantially continuous surface of living tissue. In this example, the living tissue surface would follow the shape of the lattice 20 and form a tube usable as a graft for a coronary bypass operation.

The material and section properties of both the flexible filamentary members 22 comprising the cell cultivation lattice 20 and the resilient filamentary members 14 comprising the support substrate, as well as the number of filamentary members and their method of interlacing are chosen to approximate the bending flexibility and radial compliance of a natural artery. (Radial compliance is defined as the ratio of the vessel's original diameter to its expanded diameter at maximum blood pressure and typically is about 8%.) These properties also affect the desired interstice sizes.

Preferably, the filamentary members 14 and 22 are interlaced by braiding to take advantage of the "trellis effect" associated with braided structures. The trellis effect refers to the characteristic of a braided tube to contract in diameter when the tube is stretched lengthwise by a tensile force and expand in diameter when the tube is subjected to a lengthwise applied compression force shortening the tube. The braided tube also displays complementary behavior, in that, if the diameter of the tube is contracted by application of an externally applied radial force, the tube will lengthen, and if the diameter of the tube is expanded radially outwardly, the tube will shorten in response. Radial compliance of the tubular supported lattice 10, simulating the compliance of a natural blood vessel, is thought to be best attained by the braided structure in view of the above described trellis effect which allows radial expansion and contraction of the vessel.

To provide further control over the compliance and flexibility parameters of the vessel, it is preferable to incorporate elastic elements into the cell cultivation lattice 20 by forming the flexible filamentary members 22 from elastic filaments or yarns. Textured multi-filament polyester yarns are preferred due to their compatibility with human tissue and long history of success in human implants, but other textured yarns, made from polytetrafluoroethylene, polypropylene or polyethylene may also be used. As an alternative to the textured yarns, flat yarns and filaments comprising elastic material, such as polyurethane, rubber or silicone, are also feasible.

Resilient filamentary members 14 comprising the support substrate 12 must allow for bending flexibility and radial compliance but must also contain sufficient stiffness and resilience to maintain the tubular shape of the supported lattice 10 during use. Filamentary members 14 preferably comprise stainless steel wires which have the requisite properties of stiffness and resilience, as well as compatibility with human tissue, to form the support substrate 12 which keeps the cell cultivation lattice 20 biased in the desired tubular shape. Other materials, such as nitinol, elgiloy and polypropylene, may also be used to form the filamentary members 14 comprising the support substrate 12.

An example of a tubular supported cell cultivation lattice 10 may be constructed by braiding 100 denier polyester multifilament textured yarn (flexible filamentary members 22) with 0.003 in diameter stainless steel wire (resilient filamentary members 14) over a 6 mm diameter cylindrical mandrel in the ratio of 120 yarns to 24 wires at 240 picks per linear inch. This produces a tubular vessel with acceptable bending and compliance characteristics having a cell cultivation lattice 20 with 60–80 micron sized interstices formed between the polyester yarns.

Figure 2:
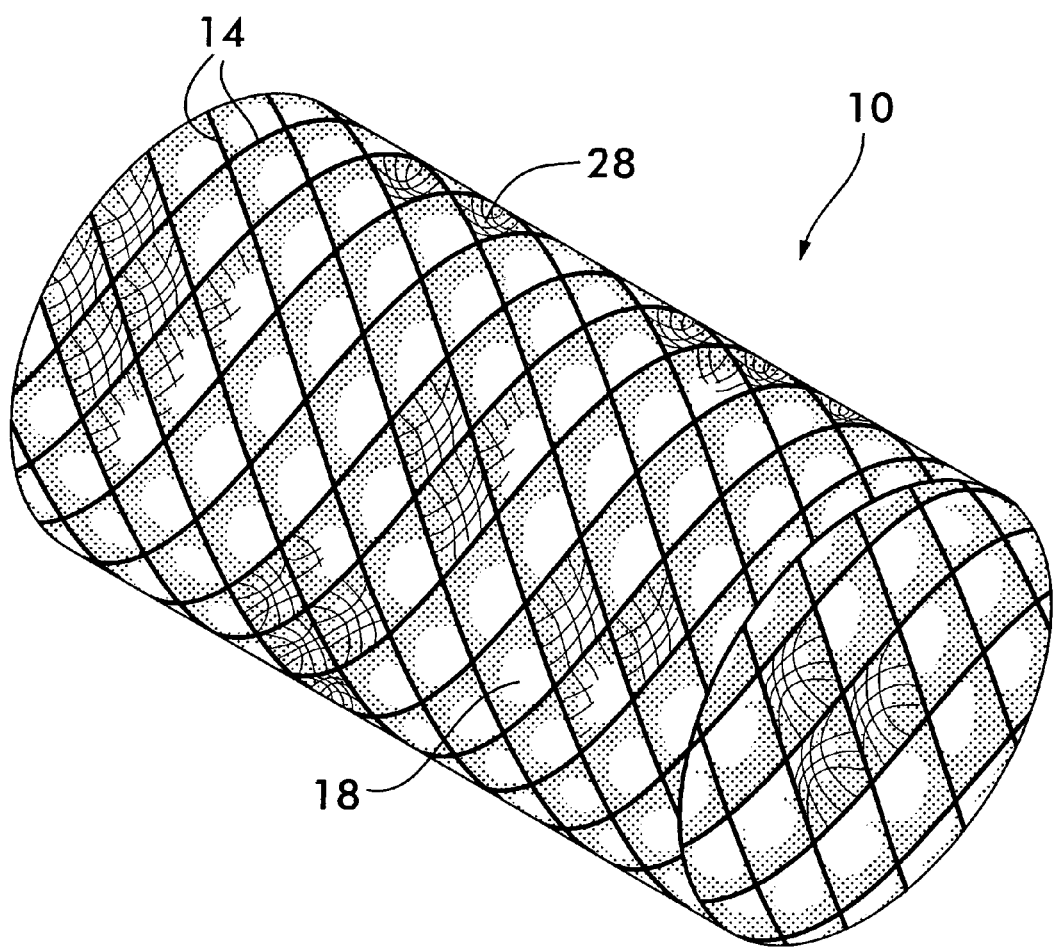
FIG. 2 shows a perspective view of another embodiment of a tubular supported lattice according to the invention.
Figure 3:
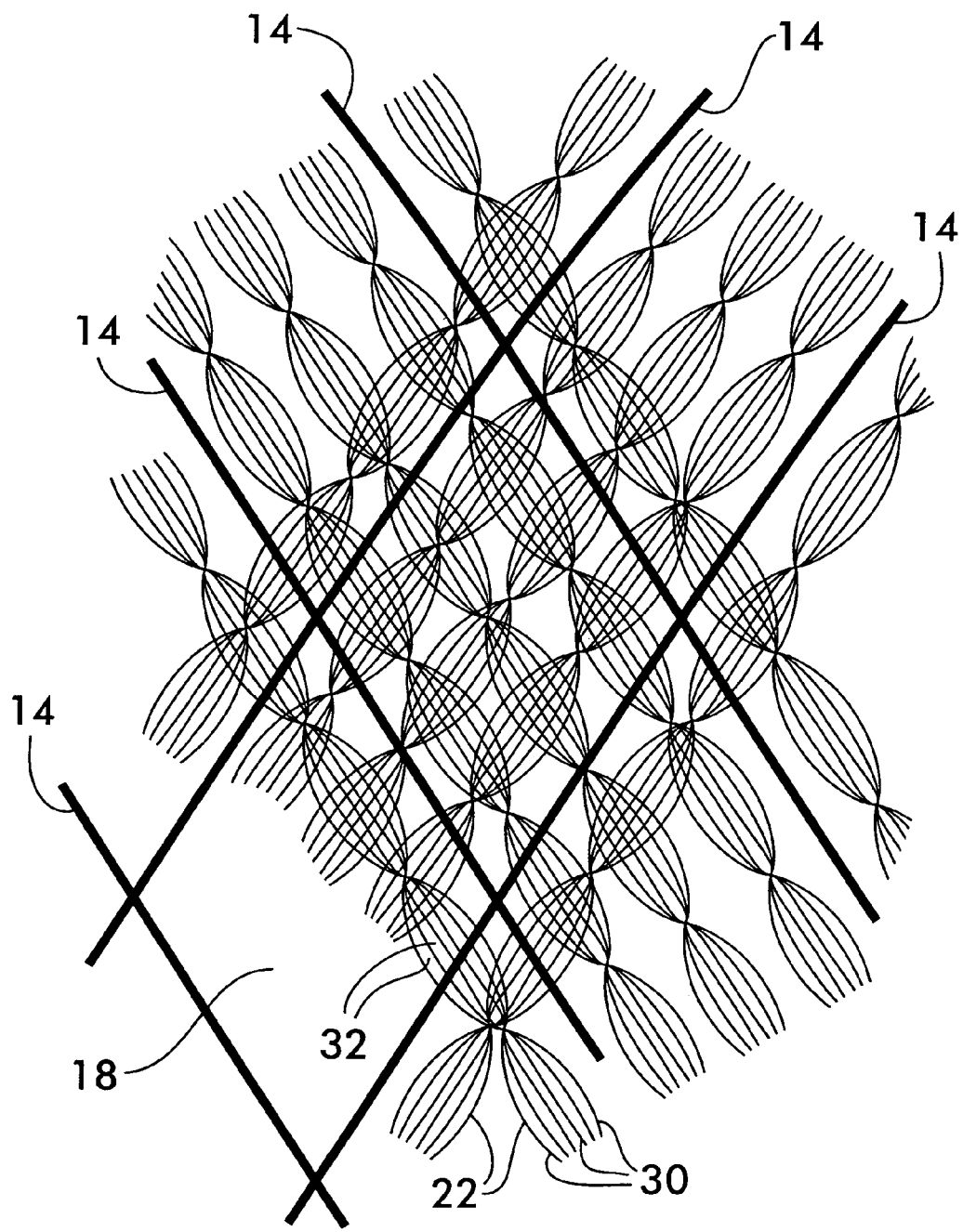
FIG. 3 shows a portion of the tubular supported lattice depicted in FIG. 2, on an enlarged scale.

Further control over the interstice size is afforded by another embodiment of the supported cell cultivation lattice 10 as describe below, again with reference to FIG. 1. In this embodiment, the cell cultivation lattice 20 is formed from flexible filamentary members 22 comprising multi-filament yarns of a material, such as polytetrafluoroethylene, which is dimensionally stable and will not expand or contract significantly when subjected to a temperature change. Resilient filamentary members 14 comprise monofilaments made from a material which shrinks when heated, such as polypropylene. The flexible filamentary members 22 and resilient filamentary members 14 are braided together over a mandrel to form the tubular supported cell cultivation lattice 10 using a ratio of flexible to resilient filamentary members which will ensure that multiple flexible filamentary members 22 are positioned over interstices 18 between adjacent resilient filamentary members 14. For example, a ratio of 120 flexible filamentary members 22 to 24 resilient filamentary members 14 will result in 5 flexible filamentary members 22 being arranged between adjacent resilient filamentary members 14 in the supported lattice 10. The supported lattice 10 is then compressed longitudinally and heated to a temperature above the melting point of the resilient filamentary members 14 and below the melting point of the flexible filamentary members 22. When compressed, the supported lattice 10 expands radially outwardly away from the mandrel due to the trellis effect associated with braided tubes. Upon heating, the resilient filamentary members 14 contract, compressing the flexible filamentary members 22 which buckle, either inwardly or outwardly, to form dimples 28, as shown in FIG. 2, in the interstices 18 between the resilient filamentary members 14 along the length of the supported lattice 10. In addition, as illustrated in FIG. 3, since the flexible filamentary members 22 comprise multi-filament yarns, the individual filaments 30 forming the yarns buckle independently of one another when compressed. As shown magnified in FIG. 3, the individual yarn filaments 30 separate outwardly and define interstices 32 which are smaller in size than can be achieved by simply braiding the lattice filaments together.

When the melting point of the resilient filamentary members 14 is reached, they fuse with one another and the flexible filamentary members 22 at the mutual cross over points in the braid. Upon cooling of the supported lattice 10, the flexible filamentary members 22 are locked into the buckled position and the supported lattice 10 comprises a cell cultivation lattice 20 formed of buckled multi-filament yarns defining relatively small interstices 32, which can be on the order of a micron or less in size. Due to the small size of the interstices, this embodiment of the supported lattice 10 may also serve as a small particle filter.

The cell cultivation lattice 20 is intended to provide a bed for the development of endothelial cells into a two-dimensional, continuous tubular tissue lining enabling the tubular supported lattice 10 to be used as a graft in a heart bypass operation. However, it is also advantageous to provide a similar cell cultivation lattice, perhaps having different properties, on the outside of the supported lattice 10 to encourage the ingrowth of body tissue after implant of the graft. Tissue ingrowth helps to fix the position of the graft preventing migration and the associated stresses on the connections between the graft and human tissue.

Figure 4:
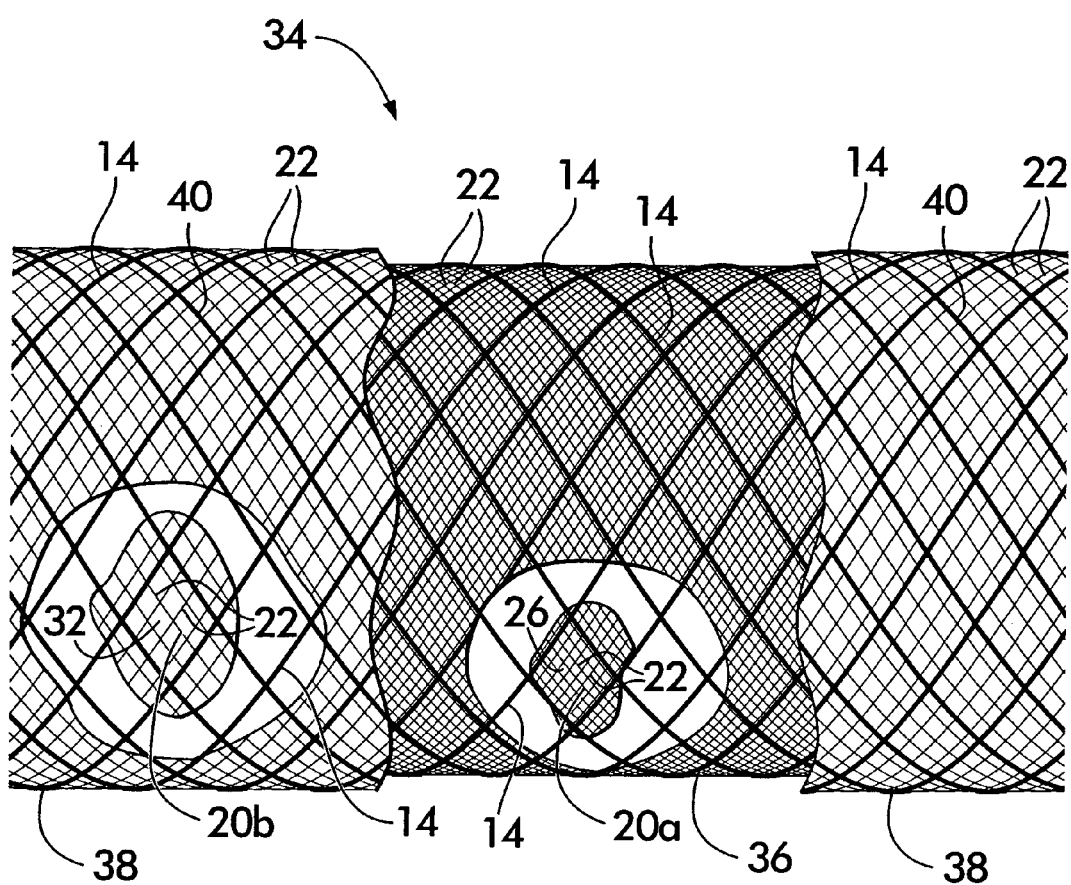
FIG. 4 shows a partial cut-away side view of another embodiment of a tubular supported lattice according to the invention.

FIG. 4 shows a tubular vessel 34 comprising an inner tubular supported lattice 36 and an outer tubular supported lattice 38 positioned coaxially surrounding the inner supported lattice 36. Each inner and outer tubular supported lattice is formed substantially as described above and comprises flexible filamentary members 22 braided with resilient filamentary members 14 to form the tubular vessel 34 having an inner cell cultivation lattice 20a and an outer cell cultivation lattice 20b.

To bind the inner and outer supported lattices together, it is preferable to incorporate into the vessel 34 bonding filamentary members 40 which have a relatively lower melting point than the flexible filamentary members 22. Bonding filamentary members 40 may comprise the resilient filamentary members 14 or may be separate filaments interbraided in one or both of the supported lattices 36 and 38 specifically to join the sleeves together. The latter configuration is preferred when it is desired to form the resilient filamentary members from metal wire, such as stainless steel or nitinol, which have inherently high melting points.

To effect a bond between the supported lattices 36 and 38, the vessel 34 is supported by a mandrel and helically wrapped with a wrapping medium to compress the supported lattices together. A filament or tape, preferably of polytetrafluoroethylene, is used as the wrapping medium, polytetrafluoroethylene being chosen so that the medium does not adhere to the vessel. Once wrapped, the vessel is subjected to a temperature above the melting point of the bonding filamentary members 40 which fuse to the filamentary members 14 and 22 comprising the inner and outer supported lattices 36 and 38 at their mutual cross over points in the braid. It has been found that if the outer supported lattice 38 is the dimpled type shown in FIG. 2, then it is necessary to use a filamentary wrapping material and wind it with a helical pitch, leaving space between each winding to allow the flexible filamentary members 22 to buckle without restraint and form the dimples 28 and interstices 32 illustrated in FIGS. 2 and 3.

An example of the tubular vessel 34 having multiple supported lattices may be made by braiding 120 polytetrafluoroethylene yarns of 100 denier to form the cell cultivation lattice 20a with 24 polypropylene monofilament resilient filamentary members 14 of 0.006 diameter over a 6 mm mandrel at 240 picks per linear inch. This will yield an inner supported lattice 36 having interstices 26 between 60 and 80 microns. Next, 120 polytetrafluoroethylene yarns of 100 denier are braided around the outside of the inner supported lattice 36 along with 24 polypropylene monofilament resilient filamentary members 14 at 100 picks per linear inch. This yields an outer supported lattice 38 having interstices 32 between 120 and 150 microns. The sleeves are helically wrapped with tape of polytetrafluoroethylene and subjected to a temperature of 190° C. for approximately 5 minutes and then cooled, causing the polypropylene to fuse together at the cross-over points and join the inner and outer supported lattices together.

The tubular supported lattice 10 according to the invention should promote the growth of endothelial cells into a substantially continuous two-dimensional tissue forming a lining which is compatible with blood, enabling the supported lattice 10 to be used as a graft in heart bypass operations. The invention promises to allow the production of blood-compatible vessels smaller than 6 mm in diameter. Using multiple supported lattices, coaxially arranged, will also allow ingrowth of tissue into the graft, fixing its position within the body.

Biodegradable Lattice for Nerve Ganglia Repair

Tubular supported lattices according to the invention, for use as blood vessel grafts for bypass operations, are formed from non-biodegradable materials and are intended to be permanent implants in the body. The strength provided by the support substrate 12 and the cell cultivation lattice 20 is necessary to enable the endothelial cells lining the lattice to withstand the repeated hydraulic pressure pulses as the heart pumps the blood through the circulatory system. However, there are other applications, such as the repair of nerve ganglia, described in detail below, in which the implant is a temporary structure in the body and is not subjected to any significant stress.

When applied to the repair of nerve ganglia, the tubular supported lattice 10, as shown in FIG. 1, comprising flexible filamentary members 22 interlaced with resilient filamentary members 14, is preferably formed of biodegradable material such as polylactic acid, polyglycolic acid and hydroxyacetic acid.

The tubular supported lattice 10, thus formed, may be surgically implanted to help mend severed nerve ganglia wherein the severed nerve ends are more than 3 mm apart and cannot be successfully stretched and sutured together. To effect the repair using the biodegradable supported lattice 10 according to the invention, the supported lattice, approximately 0.8 to 1.2 inches long and 0.1 inches in diameter, is implanted at the site of the damaged nerve, bridging the gap between the ends to be joined. Each nerve end is placed within a respective end of the supported lattice 10, which has a cell cultivation lattice 20 substantially optimally sized to promote the growth of nerve cells. The supported lattice 10 provides a bed on which the nerve cells can reproduce and also isolates the nerve ends from interference by other body tissue. The supported lattice, being made of biodegradable material, degrades and is absorbed over time, the rate of degradation being controlled by, for example, the ratio of polylactic acid to polyglycolic acid used in the filamentary members. The rate of degradation is designed such that the supported lattice will disappear when it is no longer needed, after the nerve endings have had sufficient time to grow back together.

Supported Lattice for Growth of Tissue for Skin Graft

Figure 5:
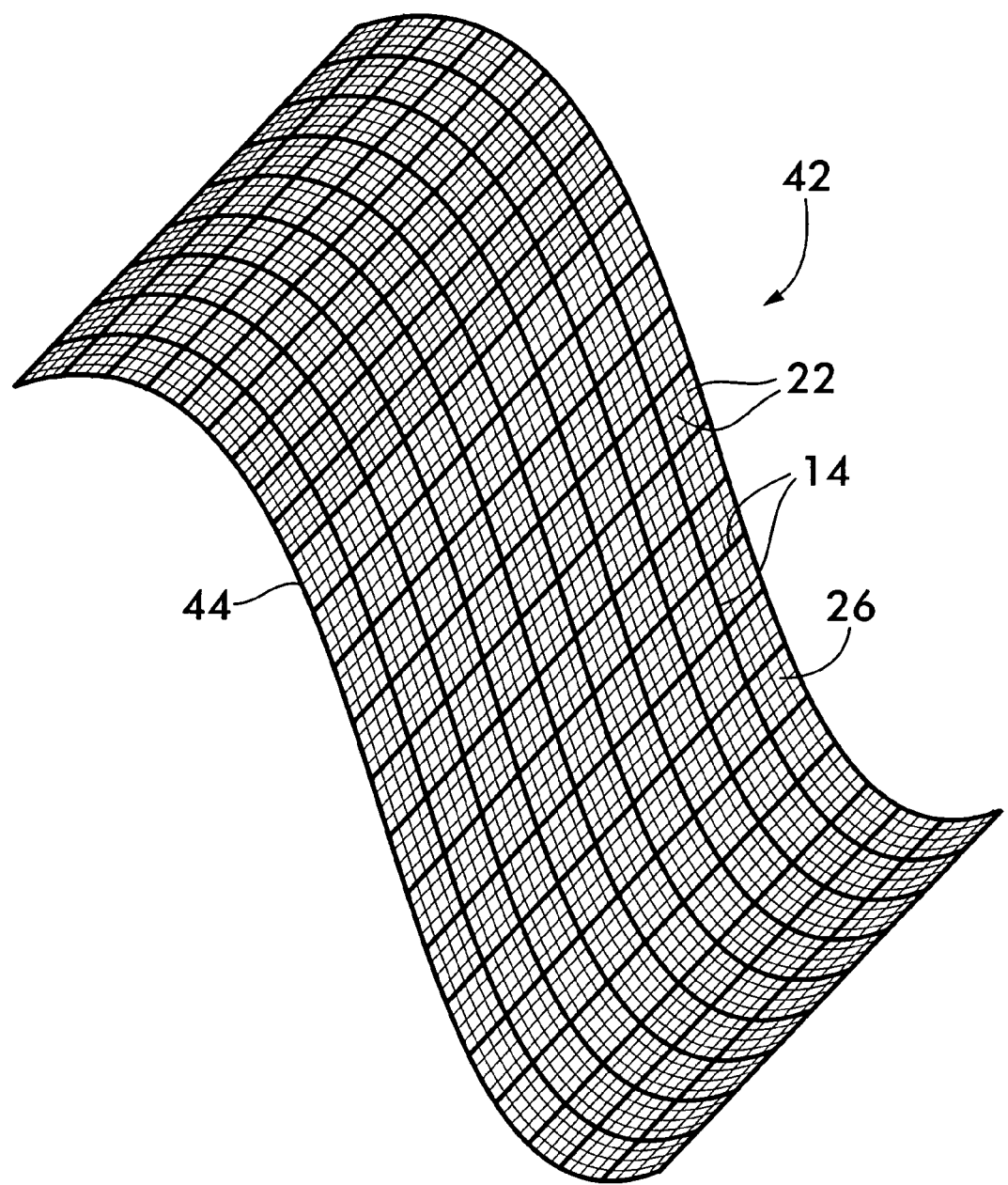
FIG. 5 shows a perspective view of an embodiment of a supported lattice having a curved shape.

A biodegradable non-tubular embodiment 42 of the supported cell cultivation lattice according to the invention is shown in FIG. 5. Lattice 42 comprises resilient filamentary members 14 intermeshed with flexible filamentary members 22 to form a flexible membrane 44 which may be shaped to match a particular contour. The filamentary members may be interlaced by weaving, knitting or braiding to form interstices 26 which promote the growth of cells in a substantially continuous, two-dimensional array throughout the supported lattice 42. Preferably, the filaments comprise biodegradable material such as polyglycolic acid, polylactic acid, hydroxyacetic acid or combinations thereof to control the rate of degradation when in use.

Supported cell cultivation lattice 42 is well suited to the cultivation of skin cells to form continuous areas of skin tissue useable as skin grafts to repair areas of skin damaged by heat, abrasion, wounds or ulceration. Donor cells may be seeded on the supported lattice 42 and grown into substantially continuous areas of skin tissue. Once formed, the skin tissue, along with the supported lattice, may be used in a grafting operation. The inherent flexibility of the supported lattice allows it to conform readily to a complex curvature of the body area onto which it is grafted. The supported lattice remains temporarily as part of the graft to provide support for the skin tissue while it takes hold. As the area heals and the support of the lattice is no longer required, it degrades and is absorbed into the body.

Lattice for Laparoscopic Hernia Repair

FIGS. 6 and 7 show another embodiment of a supported cell cultivation lattice 46 according to the invention which is also non-tubular in shape. Supported lattice 46 is formed of resilient filamentary members 14 interlaced with flexible filamentary members 22 to form a flexible sheet 48. Flexible filamentary members 22 are interlaced to form a cell cultivation lattice 20 having interstices 32 to promote cell growth. Preferably, the flexible filamentary members 22 comprise polytetrafluoroethylene, polyester or some other material which is biocompatible.

Resilient filamentary members 14 are preferably formed from a material such as stainless steel or a shape memory metal such as nitinol, either of which will provide biasing forces which will maintain the flexible sheet 48 in a desired nominal shape. The resilient filamentary members 14 may also be formed of a material having a relatively low melting point, such as polypropylene, which can be heat fused at the mutual cross over points with itself and the flexible filamentary members 22 to provide the desired biasing effect. Sheet 48 may be manipulated and held in another shape and then later released and allowed to resume its nominal shape due to the biasing action of the resilient filamentary members 14.

Supported lattice 46 according to the invention may be used in the laparoscopic repair of a hernia for example, thus, avoiding more invasive surgery currently practiced. In the laparoscopic procedure, the sheet 48 is rolled into a small diameter as illustrated in FIG. 7. The sheet is held in this shape by clamps, sutures or other means. This allows the sheet to be inserted into the small opening used in the laparoscopic procedure and positioned within the abdomen adjacent to the tear in the abdomen wall through which the intestine protrudes. Once properly located, the clamp or sutures holding the sheet are removed. Due to the biasing force provided by the resilient filamentary members 14, once released, the sheet 48 will unroll and assume the nominal flat shape illustrated in FIG. 6. The sheet may then be sutured into place, reinforcing the abdomen wall. The cell cultivation lattice 20 may have been prepared with suitable tissue for speeding the repair of the abdomen wall, or the lattice 20 may just provide support to hold the opening in the walls together and a bed for the natural ingrowth of the surrounding tissue as the opening heals.

As the abdomen tissue heals over time, it may cause a local stiffening of the tissue in the region of the repair. The sheet 48 will also add to the stiffening, which is not desired after the tissue has healed completely. Therefore, it may be desirable to include a number of biodegradable filaments 50 as part of the sheet 48. The filaments 50 will degrade and be absorbed over time, decreasing the stiffness of the sheet 48 and compensating for the natural increase in stiffness due to the formation of scar tissue as the opening in the abdomen wall heals.

The supported lattice according to the invention provides a cell cultivation lattice supported on a substrate which encourages the growth of cells to form a substantially continuous, two-dimensional array of tissue useable as a graft in various surgical procedures. The interstices of the cell cultivation lattice can be optimized in size to favor the growth of certain cell types and configured into a particular shape as required to produce a graft of substantially the same shape as the tissue which it will replace. The supported lattice promises to improve surgical procedures such as heart bypass operations, nerve mending, skin grafts and hernia repairs by reducing the trauma to the patient normally associated with those procedures.

What is claimed is:

1. A supported lattice for cultivating living cells to form living tissue, said supported lattice comprising:
   a first support substrate comprising a first elongated tube formed of a plurality of first resilient filamentary members interlaced together, said first resilient filamentary members being interlaced to form a first mesh defined by interstices that are large compared with said living cells such that said cells do not bridge said interstices;
   a first cell cultivation lattice comprising a plurality of first flexible filamentary members interlaced with one another and said first resilient filamentary members, said first flexible filamentary members being interlaced to form a second mesh defined by interstices smaller than the interstices formed by the first resilient filamentary members and adapted for growing cells in a two-dimensional array across said large interstices of said first support substrate to form a first substantially continuous surface comprising said living tissues;
   said supported lattice further comprising a second elongated tube positioned coaxially within said first elongated tube, said second elongated tube comprising:
      a second support substrate comprising a plurality of second resilient filamentary members interlaced together, said second resilient filamentary members being interlaced to form a third mesh defined by interstices that are large compared with said living cells such that said cells do not bridge said interstices; and
      a second cell cultivation lattice comprising a plurality of second flexible filamentary members interlaced with one another and said second resilient filamentary members, said second flexible filamentary members being interlaced to form a fourth mesh defined by interstices smaller than the interstices formed by the second resilient filamentary members and adapted for growing cells in a two-dimensional array across said large interstices of said second support substrate to form a second substantially continuous surface comprising said living tissue.

2. A supported lattice according to claim 1, wherein said resilient and said flexible filamentary members are interlaced by braiding.

3. A supported lattice according to claim 1, wherein said interstices between said first flexible filamentary members have an average size between about 60 microns and about 80 microns.

4. A supported lattice according to claim 1, wherein said first resilient filamentary members comprise monofilaments selected from the group consisting of stainless steel, nitinol and elgiloy monofilaments.

5. A supported lattice according to claim 4, wherein said first flexible filamentary members comprise multi-filament yarns.

6. A supported lattice according to claim 5, wherein said multi-filament yarns are elastic.

7. A supported lattice according to claim 6, wherein said multi-filament yarns comprise textured yarns.

8. A supported lattice according to claim 8, wherein said multi-filament yarns are selected from the group consisting of polyester, polytetrafluoroethylene, polypropylene and polyethylene.

9. A supported lattice according to claim 1, wherein said interstices of said first cell cultivation lattice have an average size between about 120 microns and about 150 microns and said interstices of said second cell cultivation lattice have an average size between about 60 microns and about 80 microns.

10. A supported lattice according to claim 1, further comprising a plurality of elongated filamentary bonding members interlaced with said resilient filamentary members comprising one of said elongated tubes, said filamentary bonding members having a relatively low melting point and being heat fused to said resilient filamentary members comprising said tubes, thereby joining said tubes to one another.

11. A supported lattice according to claim 1, wherein said first resilient and said first flexible filamentary members comprise bio-absorbable material selected from the group consisting of polylactic acid, polyglycolic acid and hydroxyacetic acid, said first resilient filamentary members having a relatively larger denier than said first flexible filamentary members.

12. A supported lattice according to claim 2, wherein said first resilient filamentary members comprise monofilaments selected from the group consisting of stainless steel, nitinol and elgiloy monofilaments.

13. A supported lattice according to claim 12, wherein said first flexible filamentary members comprise multi-filament yarns.

14. A supported lattice according to claim 2, wherein said first resilient filamentary members comprise a heat shrinkable material having a relatively low melting point and said first flexible filamentary members comprise multi-filament yarns of a dimensionally stable material having a relatively higher melting point, said multi-filament yarns being in a buckled configuration inwardly and outwardly from said first support substrate thereby forming dimples in said lattice, said dimples being located within said relatively large interstices between said first resilient filamentary members, said first resilient filamentary members being heat fused to one another and to said first flexible filamentary members at points of mutual contact, thereby locking said first flexible filamentary members in said buckled configuration.

15. A supported lattice according to claim 14, wherein filaments comprising said multi-filament yarns assume said buckled configuration independently of one another thereby forming relatively small interstices between said filaments.

16. A supported lattice according to claim 14, wherein said first resilient filamentary members comprise polypropylene and said first flexible filamentary members comprise polytetrafluoroethylene.

* * * * *